United States Patent
Joensen

(10) Patent No.: US 11,945,762 B2
(45) Date of Patent: Apr. 2, 2024

(54) PROCESS FOR THE CONVERSION OF LIGHT ALKANES TO AROMATIC COMPOUNDS WITH IMPROVED SELECTIVITY

(71) Applicant: HALDOR TOPSØE A/S, Kgs. Lyngby (DK)

(72) Inventor: Finn Joensen, Hørsholm (DK)

(73) Assignee: HALDOR TOPSØE A/S, Kgs. Lyngby (DK)

( * ) Notice: Subject to any disclaimer, the term of this patent is extended or adjusted under 35 U.S.C. 154(b) by 0 days.

(21) Appl. No.: 17/770,478

(22) PCT Filed: Oct. 15, 2020

(86) PCT No.: PCT/EP2020/078992
§ 371 (c)(1),
(2) Date: Apr. 20, 2022

(87) PCT Pub. No.: WO2021/078615
PCT Pub. Date: Apr. 29, 2021

(65) Prior Publication Data
US 2022/0402836 A1    Dec. 22, 2022

(30) Foreign Application Priority Data
Oct. 24, 2019  (DK) .......................... PA 2019 01251

(51) Int. Cl.
*C07C 2/84* (2006.01)
*C07C 7/148* (2006.01)
*C07C 7/20* (2006.01)

(52) U.S. Cl.
CPC ............ *C07C 2/84* (2013.01); *C07C 7/14858* (2013.01); *C07C 7/20* (2013.01); *C07C 2529/40* (2013.01)

(58) Field of Classification Search
CPC ........... C10G 50/00; C07C 2/84; C07C 7/148; C07C 7/20; B01J 29/40; B01J 29/405
See application file for complete search history.

(56) References Cited

U.S. PATENT DOCUMENTS 4,035,430 A  7/1977 Dwyer et al.
4,260,839 A  4/1981 Chen et al.
(Continued)

FOREIGN PATENT DOCUMENTS

CN  104419441 A  3/2015
CN  104447157 A  3/2015
(Continued)

OTHER PUBLICATIONS

First Technical Examination and Search Report dated Feb. 25, 2020 by the Danish Patent and Trademark Office in corresponding Danish Patent Application No. PA201901251. (8 pages).
(Continued)

*Primary Examiner* — Sharon Pregler
(74) *Attorney, Agent, or Firm* — Boone IP Law

(57) ABSTRACT

In a process for the catalytic conversion of lower hydrocarbons to aromatic compounds comprising benzene, toluene and xylenes, a process stream containing lower hydrocarbons is contacted with a zeolitic catalyst having an MFI framework and containing 0.1 to 10 percent by weight of a zinc compound. The process stream further contains one or more sulfur compounds, especially hydrogen sulfide, for improving the selectivity.

27 Claims, 3 Drawing Sheets

(56) References Cited

U.S. PATENT DOCUMENTS

Figure 1:
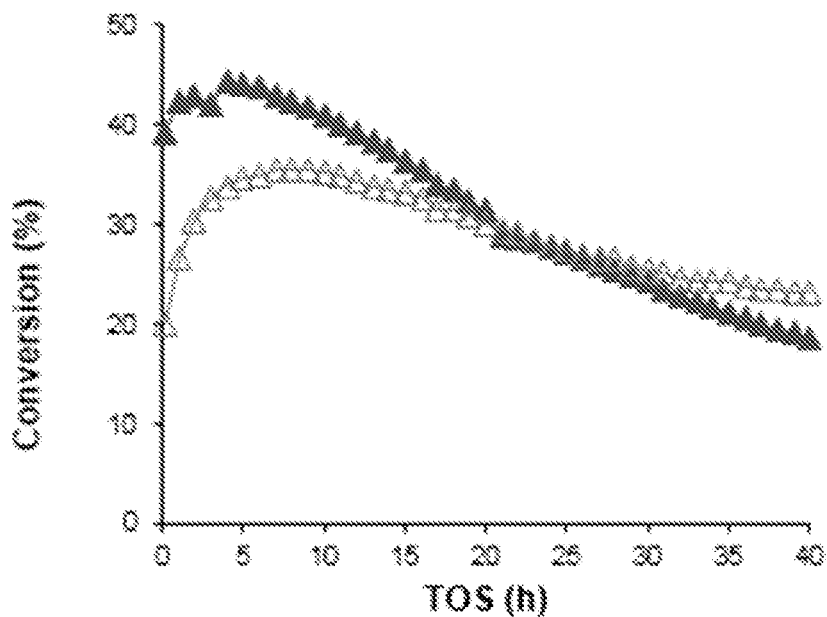

| | | | |
|---|---|---|---|
| 4,481,305 | A | 11/1984 | Jorn et al. |
| 4,520,216 | A | 5/1985 | Skov et al. |
| 4,709,113 | A | 11/1987 | Harandi et al. |
| 4,788,369 | A | 11/1988 | Marsh et al. |
| 4,835,329 | A | 5/1989 | Harandi et al. |
| 7,057,084 | B2 | 6/2006 | Nielsen et al. |
| 11,254,882 | B2 * | 2/2022 | Keusenkothen ....... C10G 50/00 |
| 2003/0118496 | A1 | 6/2003 | Nielsen et al. |
| 2005/0143610 | A1 | 6/2005 | Mitchell et al. |
| 2010/0048969 | A1 | 2/2010 | Lauritzen et al. |
| 2011/0301394 | A1 * | 12/2011 | Chen .................... B01J 37/0213 585/415 |
| 2012/0036889 | A1 | 2/2012 | Iaccino et al. |
| 2020/0231880 | A1 | 7/2020 | Rajagopalan et al. |

FOREIGN PATENT DOCUMENTS

| | | |
|---|---|---|
| CN | 104496743 A | 4/2015 |
| CN | 111518584 A | 8/2020 |
| EP | 2036970 A2 | 3/2009 |
| EP | 3110919 B1 | 5/2018 |
| WO | 2017052854 A1 | 3/2017 |
| WO | 2017052858 A1 | 3/2017 |
| WO | 2018007484 A1 | 1/2018 |
| WO | 2019/020513 A1 | 1/2019 |
| WO | 2019164610 A1 | 8/2019 |
| WO | 2019/228797 A1 | 12/2019 |
| WO | 2020150053 A1 | 7/2020 |

OTHER PUBLICATIONS

International Search Report (PCT/ISA/210) and Written Opinion (PCT/ISA/237) dated Jan. 22, 2021, by the European Patent Office as the International Searching Authority for International Application No. PCT/EP2020/078992. (10 pages).

U.S. Appl. No. 18/286,201, filed Oct. 9, 2023, Finn Joensen.

U.S. Appl. No. 18/286,472, filed Oct. 11, 2023, Finn Joensen.

Berry, R. I., "Gasoline Or Olefins From An Alcohol feed", Chemical Engineering, Access Intelligence Association, Rockville, vol. 8, No. 8, Apr. 21, 1980, pp. 86-88.

European Search Report with English translation dated Sep. 16, 2021 by the European Patent Office for European Application No. (EP 21169304.9).

International Preliminary Report on Patentability received for PCT Patent Application No. PCT/EP20/078992, dated May 5, 2022, 7 pages.

International Search Report and Written Opinion received for PCT Patent Application No. PCT/EP2022/060362, dated Aug. 18, 2022, 10 pages.

International Search Report and Written Opinion received for PCT Patent Application No. PCT/EP2022/060364, dated Aug. 12, 2022, 10 pages.

Official Action dated Nov. 8, 2021 by the Danish Patent and Trademark Office for Danish Application No. PA 2021 00392.

* cited by examiner

PROCESS FOR THE CONVERSION OF LIGHT ALKANES TO AROMATIC COMPOUNDS WITH IMPROVED SELECTIVITY

The present invention relates to a process for the conversion of light alkanes, especially low-value, ethane-rich streams, to aromatic compounds, especially high-value BTX, i.e. mixtures of benzene, toluene and xylenes, all of which are aromatic hydrocarbons. More specifically, the invention relates to a process, in which a stream, rich in ethane, can be efficiently converted into a product rich in benzene, toluene and xylenes, with only a minimum formation of higher ($C_{9+}$) aromatics and with strongly reduced selectivity to methane, in the presence of small amounts (in the order of 50 ppm) of sulfur, e.g. $H_2S$. The preferred catalyst comprises a zeolite, preferably of MFI-type, containing from 0.1-10 wt % Zn and, optionally, from 1-5 wt % of a phosphorus compound. The zeolite is preferably embedded in a binder matrix, such as alumina.

Natural gas mainly contains methane and smaller amounts of ethane, propane, butane and heavier hydrocarbons along with varying amounts of water vapor, carbon dioxide, sulfur compounds and other non-hydrocarbons. Ethane, propane, butane and propane are known as associated gases. The removal of these gases from raw natural gas may be desirable to meet consumer specifications of natural gas or to obtain individual hydrocarbons from natural gas. Various techniques, such as compression, refrigeration, absorption, adsorption or combinations of those, can be used to recover associated gases from natural gas.

Recovery of natural-gas liquids (NGL) from natural gas is quite common in natural gas processing. Recovery is usually done with the purpose of:
  producing transportable gas (containing a sufficiently low amount of heavier hydrocarbons to avoid condensation in the pipeline),
  meeting a sales gas specification and/or
  maximizing liquid recovery (when liquid products are more valuable than methane).

Natural gas liquids (NGLs) are hydrocarbons belonging to the same family of molecules as natural gas and crude oil. They are composed exclusively of carbon and hydrogen except for minute amounts of e.g. carbon dioxide and sulfur compounds. Lower alkanes above methane, i.e. ethane, propane, n-butane, isobutane and pentane, are all NGLs. There are many uses for NGLs, spanning nearly all technical areas. NGLs can be used as inputs for petrochemical plants, they can be burned for heating and cooking purposes, and they can be blended into vehicle fuels. High NGL values have provided incentives to drill in liquids-rich resources with significant NGL contents.

The chemical composition of these individual hydrocarbons is similar, yet their fields of application vary widely. Ethane occupies the largest share of NGL field production. The majority is used to produce ethylene, which can then be turned into plastics. Much of the propane, by contrast, is burned for heating purposes, although a substantial amount is used as petrochemical feedstock. A blend of propane and butane, called LPG, is a quite popular fuel in some parts of Europe and Asia. Natural gasoline ($C_{5+}$) can be blended into various kinds of fuel for combustion engines, and it is also useful in energy recovery from wells and oil sands.

NGLs can be removed from raw natural gas by various gas processing techniques. These NGLs are ethane ($C_2$), propane ($C_3$), butane ($C_4$) and pentane plus ($C_{5+}$, natural gasoline) found in natural gas. The mixture of NGLs can be separated into the individual compounds by fractionation.

Normally also, sulfur is removed since it is regarded as an impurity i.e. contaminant for downstream catalytic processes.

The present invention discloses a catalyst and a process, by which a stream rich in ethane can be efficiently converted into a BTX product with only minimum formation of higher ($C_{9+}$) aromatics and with a strongly reduced selectivity to methane in the presence of small amounts (about 50 ppm) of sulfur, e.g. as $H_2S$.

With the present invention, it becomes possible to convert ethane of low value to a liquid product, which is rich in aromatic compounds, and a gaseous product, which is rich in ethylene, thereby providing an outlet for ethane-rich streams, which are in considerable surplus due to shale gas production of natural gas. Ethylene itself is a valuable product, which may either be separated from the effluent, or it may be recycled to the reactor where it will, eventually, be converted into aromatics.

The standard solution regarding what to do with the surplus ethane consists in feeding the ethane to steam crackers for making ethylene. However, steam crackers are capital extensive and, moreover, the market is already over-saturated with surplus ethane. Some of this ethane is liquefied and exported, or simply used as fuel. It may be converted to BTX over e.g. Zn/ZSM-5 catalysts, although this approach has not yet reached commercial scale. This is possibly due to the fact that appreciable amounts of heavy aromatics, e.g. $C_{9+}$ aromatics, are formed as by-products.

According to the invention, the preferred catalyst comprises a zeolite, preferably of MFI type, containing 0.1-10 wt % Zn and, optionally, 1-5 wt % P. The zeolite is preferably embedded in a binder matrix, such as alumina.

The technical features of the process of the invention can be summarized as follows: Temperature T: 550-600° C.; pressure P: 3-20 bar abs.; 10-100 ppm S in feed stream; optionally, recycle of unconverted olefins.

Regarding prior art, US 2012/0036889 describes a process for converting a methane feed to an aromatic hydrocarbon, said process being integrated with LNG and/or pipeline gas production. The hydrocarbon feed is supplied to a conversion zone comprising a dehydroaromatization catalyst, where it is converted to a gaseous effluent comprising at least one aromatic compound, unreacted methane and hydrogen. The effluent is separated into a first stream comprising the at least one aromatic compound and a second stream comprising methane and hydrogen. The methane is passed to LNG and/or pipeline gas production. The gaseous hydrocarbon feed has at least one of the following properties: (i) a sulfur level of at least 25 ppmv, (ii) a $CO_2$ level of at least 25 ppmv and (iii) a dew point of at least −70.15° C. Preferred catalysts used in the conversion zone include Mo, W, Zn, Re and compounds and combinations thereof supported on ZSM-5, silica or alumina.

A process for the removal of higher hydrocarbons from natural gas further containing sulfur compounds is described in U.S. Pat. No. 7,057,084 B2 belonging to the applicant. The process is based on simultaneous conversion of the hydrocarbons to aromatic compounds and methane using specific crystalline aluminosilicates as catalysts for the removal of higher hydrocarbons from natural gas by conversion (aromatization), allowing a subsequent separation of the aromatized molecules from methane.

A process for converting C1-C4 alkanes to aromatic compounds, such as BTX, using a catalyst of a crystalline zeolite, on which platinum has been deposited, is described in US 2005/0143610 A1. The catalyst can specifically be a Pt-containing ZSM-5 catalyst, which suppresses the formation of methane and increases the selectivity to BTX. The high content of ethane relative to methane in the light gas fraction allows the process effluent to be the feed stream for a steam cracker.

EP 3 110 919 B1 describes a process for producing BTX from a mixed hydrocarbon stream, which comprises pyrolysis, aromatic ring opening and recovery of the BTX produced.

Applicant's own US 2003/0118496 A1 discloses a process for the removal hydrocarbons from natural gas, which further contains sulfur compounds, by simultaneous conversion of the hydrocarbons to aromatic compounds and methane in the presence of a catalyst comprising a crystalline alumino silicate, such as a H-ZSM-5 zeolite.

US 2010/0048969 A1 discloses a process for producing aromatics from lower alkanes with reduced production of methane by using a zeolite catalyst such as ZSM-5 comprising Pt and an attenuating metal consisting of tin, lead and germanium.

US 2011/0301394 A1 discloses a fixed bed process for the aromatization of lower alkanes using a catalyst diluted with a second inert solid material.

WO 2019/164610 A1 discloses an overall process for conversion of a raw natural gas feed comprising hydrogen sulfide and ethane to aromatics, in particular by upgrading light hydrocarbon streams that do not remove methane and/or ethane from the light hydrocarbon stream before catalytic processing. The conversion results in products having greater concentrations of methane than the feed, but lesser concentration of ethane. This citation is therefore silent at least about how to suppress the formation of methane in the aromatic formation process.

WO 2017/052858 A1 discloses an overall process for converting alkanes such as a feed containing ethane while generating improved selectivity to desired aromatics, whereby aromatics generated in a first stage (aromatic formation process), in particular benzene, are further alkylated to form xylenes. A number of feeds containing alkanes are cited, one being a feed comprising less than 10 wt % hydrogen sulfide as impurity. This citation is at least silent about how to improve the selectivity to BTX and how to suppress the formation of methane and $C_{9+}$ aromatics in the aromatic formation process.

The effects and advantages of the present invention can be summarized as an improved selectivity to BTX end product with minimum formation of methane and $C_{9+}$ aromatics (indanes/indenes and naphthalenes).

Aromatization of hydrocarbons is an endothermic reaction, and it has been proposed to carry out exothermic hydrocracking and endothermic aromatic synthesis simultaneously in a catalytic reaction zone according to the following reaction, taking propane as an example of the higher hydrocarbons to be removed from natural gas:

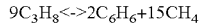

9C$_3$H$_8$<->2C$_6$H$_6$+15CH$_4$

The reaction is substantially thermo-neutral with an enthalpy of −5 kcal/mole.

The above simultaneously endo- and exothermic reaction has been applied and mentioned in U.S. Pat. No. 4,260,839 for ethane conversion in production of LPG, gasoline and aromatics by contact with a catalyst of ZSM-5 type.

The method according to the present invention consists in subjecting raw natural gas to a gas processing procedure in a manner known per se, thereby obtaining pure methane and Y-grade NGLs. However, instead of said NGLs being subjected to fractionation, they are used as feed for an aromatic synthesis process leading to a mixture of valuable aromatic compounds, more specifically—and mainly—benzene, toluene and xylenes, as well as a further amount of methane which can either be added to the pure natural gas from the gas processing procedure, if necessary after a purifying treatment, or be used separately for other purposes, such as energy production. It may sometimes be more economically attractive to subject at least part of the feed gas to aromatization in the presence of an aromatization catalyst, thereby converting the NGLs in the feed gas to a mixture of aromatic compounds, instead of fractionating the NGLs the traditional way.

Even though NGL stands for a natural gas liquid, this does not mean that all natural gas liquids originate from raw natural gas. In fact, the term "natural gas liquid" specifically refers to the lighter (yet heavier than methane), condensable hydrocarbon fractions of the hydrocarbon stream in question. These "lighter" hydrocarbons are those with only a few carbon atoms. Methane is the lightest hydrocarbon fraction, having only one carbon atom in the molecule. Nevertheless, methane is not an NGL because it cannot be condensed during normal processes, which is due to its very low boiling point of −164° C.

Hydrocarbons are often classified as "X-grade" or "Y-grade" hydrocarbons. Y-grade is a common term in the industry for the "easily" condensable hydrocarbons. Both X-grade and Y-grade hydrocarbons can be stored in a liquid state under pressure, but Y-grade hydrocarbons can be stored at a pressure much less than that required for X-grade ones, which makes the Y-grade hydrocarbons easier to move in a liquid state.

Specifically, the present invention relates to a process for the catalytic conversion of gas mixtures of lower hydrocarbons, which contain at least 50% by volume of ethane, to aromatic compounds consisting essentially of, i.e. comprising, benzene, toluene and xylenes, said process comprising contacting a process stream containing lower hydrocarbons with a zeolitic catalyst having an MFI framework and containing 0.1 to 10 percent by weight of zinc, wherein the process stream further contains one or more sulfur compounds.

It would be understood that the term "lower hydrocarbons" refer to lower alkanes above methane, i.e. ethane, propane, n-butane, isobutane and pentane, and optionally also $C_{5+}$ (natural gasoline) found in natural gas; all being NGLs.

It would also be understood that the % by volume of ethane of the gas mixture is with reference to the other lower hydrocarbons therein, i.e. without including a diluent such as nitrogen ($N_2$). It would also be understood that the term "process stream" means the feed stream in the process which contains the lower hydrocarbons and may include a diluent such as $N_2$. For instance, a process stream containing lower hydrocarbons as 10% by volume of ethane ($C_2H_6$) in $N_2$ means 100 percent by volume ethane in the gas mixture of lower hydrocarbons, and 10 percent volume ethane in the process stream.

Accordingly, the invention can also be recited as a process for the catalytic conversion of a process stream containing lower hydrocarbons, to aromatic compounds comprising benzene, toluene and xylene e.g. a mixture of benzene, toluene and xylene (BTX), by contacting said process stream with a zeolitic catalyst having an MFI framework and containing 0.1 to 10 percent by weight of a zinc compound, said process stream comprising a gas mixture of lower hydrocarbons which contains at least 50% by volume of ethane, and wherein the process stream further contains one or more sulfur compounds.

Preferably, the content of the one or more sulfur compounds is 10-100 ppm.

For the purposes of the present application, ppm units are in a volume basis, i.e. ppmv.

Preferably, the process further comprises forming a gas stream effluent of unconverted olefins and recycling at least a portion thereof back to the process. This enables increasing the BTX-yield in the process.

Hence, the process generates not only the aromatic compounds comprising benzene, toluene and xylenes (BTX), but also a gas stream effluent of unconverted olefins. The gas stream of unconverted olefins is for instance an ethylene-rich stream, e.g. a stream comprising 90% vol. or more ethylene. Ethylene itself is a valuable product, which may either be separated from the gas stream effluent, or it may be recycled to the process as described above where it will, eventually, be converted into aromatics.

Optionally, the catalyst may contain Cu instead of Zn or it may contain mixtures of copper and zinc.

Preferably, the zeolite catalyst is ZSM-5, and the zinc compound is metallic and/or oxidic zinc. In a preferred embodiment, the zeolite catalyst is embedded in a binder matrix. This binder matrix may advantageously comprise alumina.

According to another preferred embodiment, the zeolite further contains 1 to 5 percent by weight of a phosphorus compound, e.g. 1-5 wt % P.

According to a specific embodiment, the zeolite catalyst is ZSM-5, contains 0.1-10 wt % Zn and, optionally, 1-5 wt % P.

In another specific embodiment, the zeolite catalyst comprises 5 wt % Zn supported on H-ZSM-5 having a silica to alumina ratio of 40.

Preferably, the feed stream in the process contains 90 to 100 percent by volume ethane. Accordingly, in an embodiment of the invention the process stream contains 90 to 100 percent by volume ethane. Further, it is preferred that the one or more sulfur compounds in the process stream is $H_2S$, for instance 10-100 ppm $H_2S$ According to another preferred embodiment, the process is conducted at a temperature in the range 550-600° C., and pressure in the range 3-20 bar abs.

In another preferred embodiment, the weight hour space velocity (WHSV) is in the range 2-6, for instance 3.

In yet another preferred embodiment, the process stream containing lower hydrocarbons is derived from subjecting raw natural gas to a gas processing step selected from compression, refrigeration, absorption, adsorption or combinations thereof, thereby obtaining pure methane and said process stream. The process stream will normally be free of sulfur compounds and thus the one or more sulfur compounds need to be added.

Accordingly, in another preferred embodiment, the one or more sulfur compounds are added to the process stream.

The mixture of organic compounds, primarily consisting of benzene, toluene and xylenes, i.e. the aromatic compounds produced by the process of the present invention can be fractionated to obtain pure grade benzene, toluene and xylene products. These products can subsequently be upgraded, e.g. to obtain o-, m- and p-xylenes, or they may be applied as feed or part of the feed in processes for producing p-xylene.

Besides being present as part of the NGLs obtained from gas processing of raw natural gas, $C_{5+}$ fractions may also originate from processing plants within various industries. For instance, a heavy $C_{5+}$ stream is obtained as a by-product in ethylene production through pyrolysis (steam cracking). This $C_{5+}$ stream is referred to in the industry as pyrolysis gasoline or pygas. Left in its raw form, said $C_{5+}$ stream has little commercial value owing to its high reactivity and low stability. However, the stream contains many high-value components, such as isoprene, benzene, toluene and xylenes.

Another option is therefore to add the mixture of organic compounds (mixture of benzene, toluene and xylene, i.e. BTX), which is produced by the process of the present invention, to a similar mixture of organic compounds obtained by extraction of pygas instead of fractionating the mixture directly. The pygas may come from an existing processing plant, such as a steam cracking plant. The resulting mixture of organic compounds from the process of the invention and from an existing plant can subsequently be fractionated as described above to obtain pure grade benzene, toluene and xylene products.

Accordingly, in another embodiment, the process further comprises combining said aromatic compounds comprising benzene, toluene and xylene, with a pyrolysis gasoline (pygas) obtained as a by-product in a separate ethylene production through steam cracking, thereby forming a combined stream comprising benzene, toluene and xylene, and optionally subsequently subjecting the combined stream to one or more fractionation steps for producing pure grade benzene, toluene and xylene products.

The invention is illustrated further in the example which follows. The C2-C5 fractions from mixed gas sources, such as shale gas, are valuable hydrocarbon feeds for synthetizing a mixture of aromatic compounds by aromatization of Y-grade natural gas liquids. Among the C2-C5 hydrocarbons, the most difficult one to convert is ethane ($C_2H_6$).

As mentioned above, BTX is a valuable aromatic product that may be used as a feed for the production of p-xylene. It may also be applied as a high-octane reformate for gasoline blending. In contrast to BTX, aromatics with higher carbon numbers, i.e. $C_{9+}$, are considered less valuable. Consequently, in a process for making aromatics, a high selectivity to BTX is desirable.

As illustrated in the example, conversion of ethane leads to the formation of appreciable amounts of methane and higher aromatics, i.e., aromatics with carbon numbers 9 and higher. These higher aromatics are predominantly napthtalenes, such as 1- and 2-methylnaphthalene and indanes and indenes as well as methyl-substituted indanes/indenes which are mixtures of little value.

By actively adding a small amount of sulfur (as $H_2S$) to the ethane feed stream (process stream), the selectivity towards methane and $C_{9+}$ hydrocarbons is greatly suppressed, as illustrated in Example 1.

EXAMPLE

Catalyst: 5 wt % Zn supported on H-ZSM-5 having a silica to alumina ratio of 40.

Conditions: 550° C., 3 bar abs., WHSV=3, 10 vol % $C_2H_6$ in $N_2$.

In the figures are shown ethane conversion and product selectivity over time on stream (TOS); closed symbols are results without $H_2S$, i.e. without $H_2S$ being added; open symbols are results with 60 ppm $H_2S$ in the feed.

The figures reveal that the conversion over time is essentially the same with and without $H_2S$ in the feed (FIG. 1). In particular, it is noted that the conversion in the presence of $H_2S$ is lower in the beginning, but soon (after about 20 hours) surpasses the conversion of the same catalyst operating under sulfur-free conditions.

Figure 2:
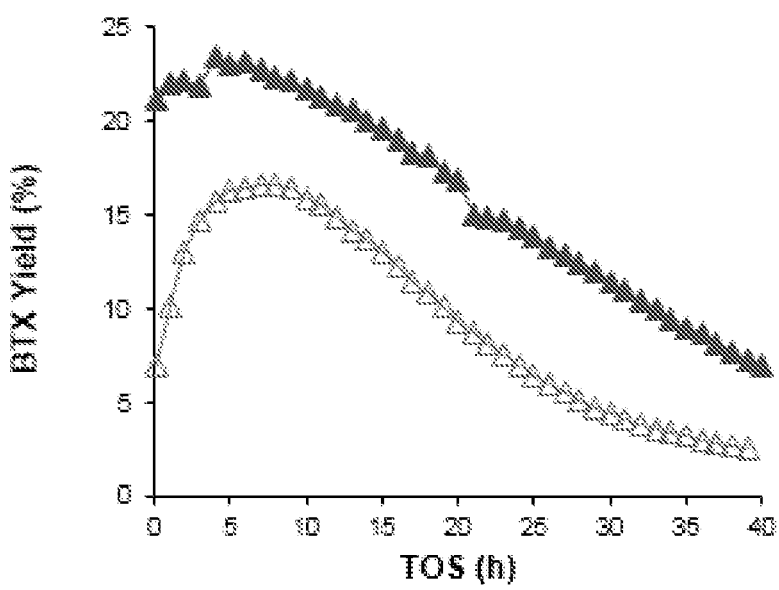
Figure 3:
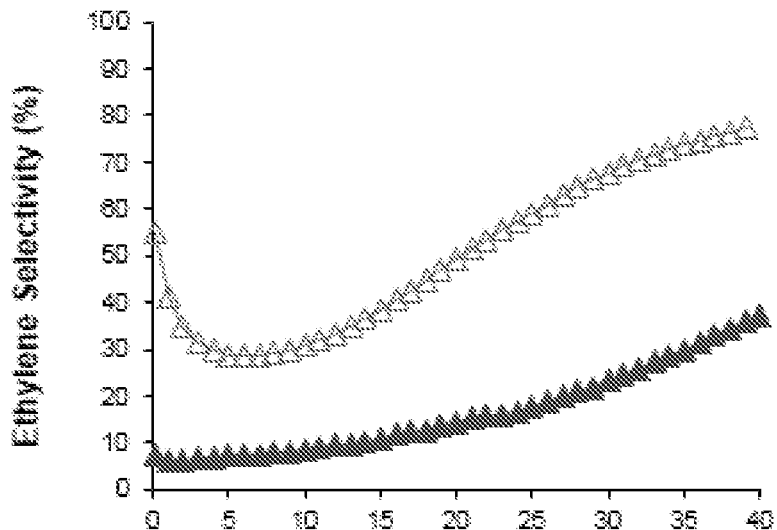
Figure 4:
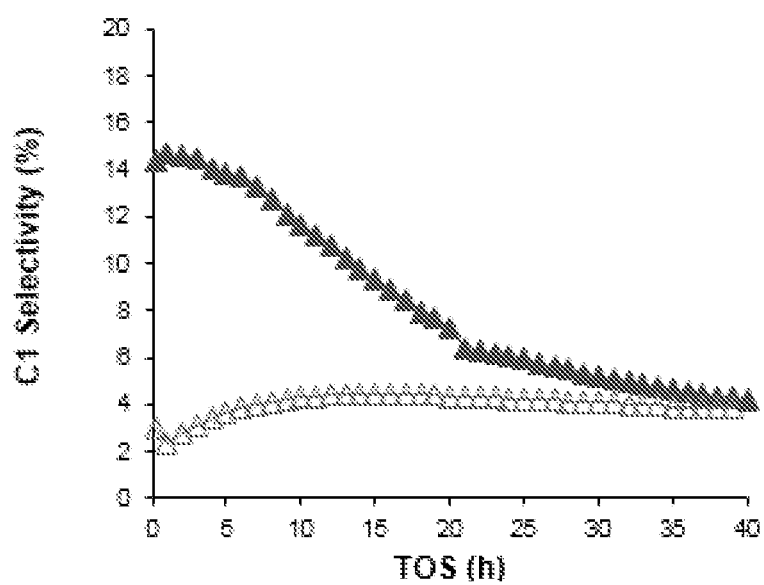
Figure 5:
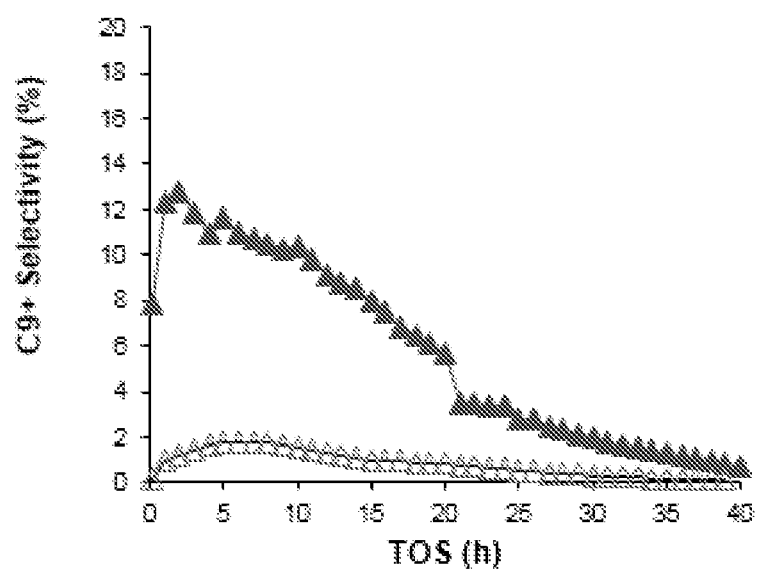

The BTX yield with $H_2S$ in the feed is somewhat lower (FIG. 2), but the selectivity to ethylene (and other light olefins) is significantly higher with $H_2S$ in the feed (FIG. 3). Further it is seen that the methane (FIG. 4) and $C_{9+}$ (FIG. 5) selectivities are dramatically lower in the presence of $H_2S$.

The invention claimed is:

1. A process for the catalytic conversion of gas mixtures, said process comprising:
    contacting a process stream with a zeolitic catalyst, the zeolitic catalyst having an MFI framework and comprising 0.1 to 10 percent by weight of a zinc compound; and
    converting at least part of the process stream to aromatic compounds comprising benzene, toluene and xylenes,
    wherein the process stream comprises lower hydrocarbons and one or more sulfur compounds, wherein the lower hydrocarbons are at least 50% by volume of ethane,
    wherein at least one selectivity of the following is achieved:
        the selectivity of methane does not exceed 5%,
        the selectivity of aromatics with nine or more carbon atoms does not exceed 2%, or
        the selectivity of ethylene is at least 30%.

2. The process of claim 1, wherein the content of the one or more sulfur compounds in the process stream is 10-100 ppm.

3. The process of claim 1, further comprising forming a gas stream effluent of unconverted olefins and recycling at least a portion thereof back to the process.

4. The process of claim 1, wherein the zeolite catalyst is ZSM-5.

5. The process of claim 1, wherein the zinc compound is metallic and/or oxidic zinc.

6. The process of claim 1, wherein the zeolite further comprises 1 to 5 percent by weight of a phosphorus compound.

7. The process of claim 1, wherein the zeolite catalyst is embedded in a binder matrix.

8. The process of claim 7, wherein the binder matrix comprises alumina.

9. The process of claim 1, wherein the process stream comprises 90 to 100 percent by volume ethane.

10. The process of claim 1, wherein the sulfur compound is $H_2S$.

11. The process of claim 1, wherein the temperature is in the range 550-600° C., and the pressure is in the range 3-20 bar abs.

12. The process of claim 1, wherein the process stream is derived from subjecting raw natural gas to a gas processing step selected from compression, refrigeration, absorption, adsorption or combinations thereof, thereby obtaining pure methane and said process stream.

13. The process of claim 1, wherein the one or more sulfur compounds are added to the process stream.

14. The process of claim 1, further comprising combining said aromatic compounds comprising benzene, toluene and xylene, with a pyrolysis gasoline obtained as a by-product in a separate ethylene production through steam cracking, thereby forming a combined stream comprising benzene, toluene and xylene, and optionally subsequently subjecting the combined stream to one or more fractionation steps for producing pure grade benzene, toluene and xylene products.

15. The process of claim 1, wherein the selectivity of methane does not exceed 5%.

16. The process of claim 1, wherein the selectivity of aromatics with nine or more carbon atoms does not exceed 2%.

17. The process of claim 1, wherein the selectivity of ethylene is at least 30%.

18. A process for the catalytic conversion of gas mixtures of lower hydrocarbons, which contain at least 50% by volume of ethane, to aromatic compounds comprising benzene, toluene and xylenes, said process comprising the steps of contacting a process stream containing lower hydrocarbons with a zeolitic catalyst having an MFI framework and containing 0.1 to 10 percent by weight of a copper compound, wherein the process stream further contains one or more sulfur compounds,
    wherein at least one selectivity of the following is achieved:
        the selectivity of methane does not exceed 5%,
        the selectivity of aromatics with nine or more carbon atoms does not exceed 2%, or
        the selectivity of ethylene is at least 30%.

19. The process of claim 1, the process comprising adding one or more sulfur compounds to a pre-process stream to obtain the process stream.

20. The process of claim 1, wherein the process stream further comprises a diluent.

21. The process of claim 20, wherein the diluent is $N_2$.

22. The process of claim 1, wherein the process stream further comprises methane.

23. The process of claim 1, wherein the process stream consists of lower hydrocarbons, one or more sulfur compounds, and, optionally, a diluent.

24. A process for the catalytic conversion of gas mixtures, said process comprising:
    contacting a process stream with a zeolitic catalyst, the zeolitic catalyst having an MFI framework and comprising 0.1 to 10 percent by weight of a zinc compound; and
    converting at least part of the process stream to aromatic compounds comprising benzene, toluene and xylenes,
    wherein the process stream comprises lower hydrocarbons and one or more sulfur compounds, wherein the lower hydrocarbons are at least 50% by volume of ethane,
    wherein the process stream is derived from subjecting raw natural gas to a gas processing step selected from compression, refrigeration, absorption, adsorption, or combinations thereof, thereby obtaining pure methane and said process stream,
    wherein the one or more sulfur compounds are added to the process stream.

25. The process of claim 18, wherein the selectivity of methane does not exceed 5%.

26. The process of claim 18, wherein the selectivity of aromatics with nine or more carbon atoms does not exceed 2%.

27. The process of claim 18, wherein the selectivity of ethylene is at least 30%.

* * * * *